(12) United States Patent
Tseng et al.

(10) Patent No.: US 10,426,602 B2
(45) Date of Patent: Oct. 1, 2019

(54) INTRAOCULAR LENS (IOL) INJECTOR AND METHOD OF USE THEREOF

(71) Applicant: AST PRODUCTS, INC., Billerica, MA (US)

(72) Inventors: Wen-Chu Tseng, Westford, MA (US); Ming-Yen Shen, Keelung (TW); William Lee, Chelsea, MA (US)

(73) Assignee: AST Products, Inc., Billerica, MA (US)

( * ) Notice: Subject to any disclaimer, the term of this patent is extended or adjusted under 35 U.S.C. 154(b) by 203 days.

(21) Appl. No.: 15/725,993

(22) Filed: Oct. 5, 2017

(65) Prior Publication Data
US 2019/0105151 A1   Apr. 11, 2019

(51) Int. Cl.
  *A61F 2/16* (2006.01)
  *A61B 50/30* (2016.01)

(52) U.S. Cl.
  CPC ............ *A61F 2/167* (2013.01); *A61F 2/1678* (2013.01); *A61F 2/1691* (2013.01); *A61B 50/30* (2016.02); *A61F 2/1667* (2013.01)

(58) Field of Classification Search
  CPC ...... A61F 2/167; A61F 2/1678; A61F 2/1691; A61F 2/1667; A61B 50/30
  See application file for complete search history.

(56) References Cited

U.S. PATENT DOCUMENTS

| | | | |
|---|---|---|---|
| 5,494,484 A | 2/1996 | Feingold | |
| 9,326,847 B2* | 5/2016 | Sanger | A61F 2/1672 |
| 9,549,813 B2* | 1/2017 | Anderson | A61F 2/167 |
| D789,520 S * | 6/2017 | Tseng | D24/114 |
| 9,687,340 B2* | 6/2017 | Anderson | A61F 2/167 |
| 9,700,407 B2* | 7/2017 | Safabash | A61F 2/1678 |
| D836,771 S * | 12/2018 | Tseng | D24/112 |
| 10,226,328 B2* | 3/2019 | Fayyaz | A61F 2/167 |
| 2004/0147938 A1* | 7/2004 | Dusek | A61F 2/1664 606/107 |
| 2005/0049606 A1 | 3/2005 | Vaquero et al. | |
| 2005/0222578 A1* | 10/2005 | Vaquero | A61F 2/1678 606/107 |
| 2008/0221584 A1* | 9/2008 | Downer | A61F 2/1678 606/107 |
| 2009/0024136 A1* | 1/2009 | Martin | A61F 2/1664 606/107 |
| 2009/0131953 A1 | 5/2009 | Quintin et al. | |
| 2009/0312767 A1 | 12/2009 | Pollock | |
| 2009/0318933 A1* | 12/2009 | Anderson | A61F 2/1664 606/107 |

(Continued)

OTHER PUBLICATIONS

International Search Report dated Dec. 28, 2017, regarding PCT/US2017/055339.

*Primary Examiner* — Phong Son H Dang
(74) *Attorney, Agent, or Firm* — DLA Piper LLP (US)

(57) ABSTRACT

The present invention provides a device and method for inserting an IOL into an eye of a patient. The IOL injector is configured to automatically load an IOL into the injector by folding and aligning the IOL into a lens cartridge of the injector without manual manipulation of the IOL by the physician during the procedure. The injector is configured to properly orient and align the IOL within the injector and maintain proper alignment throughout delivery of the IOL to the eye of a patient and thereby ensuring that the IOL is properly positioned and oriented at a predetermined location in the eye.

20 Claims, 13 Drawing Sheets

(56) References Cited

U.S. PATENT DOCUMENTS

| | | | |
|---|---|---|---|
| 2010/0106160 A1 | 4/2010 | Tsai | |
| 2010/0185206 A1* | 7/2010 | Ichinohe | A61F 2/1672 606/107 |
| 2010/0217273 A1* | 8/2010 | Someya | A61F 2/1678 606/107 |
| 2010/0256651 A1 | 10/2010 | Jani et al. | |
| 2010/0286704 A1* | 11/2010 | Ichinohe | A61F 2/1667 606/107 |
| 2011/0082463 A1* | 4/2011 | Inoue | A61F 2/1664 606/107 |
| 2011/0245840 A1* | 10/2011 | Seyboth | A61F 2/1678 606/107 |
| 2012/0289969 A1* | 11/2012 | Seyboth | A61F 2/1678 606/107 |
| 2013/0006259 A1* | 1/2013 | Sanger | A61F 2/1672 606/107 |
| 2013/0226193 A1* | 8/2013 | Kudo | A61F 2/148 606/107 |
| 2014/0012277 A1* | 1/2014 | Matthews | A61F 2/1675 606/107 |
| 2014/0200588 A1* | 7/2014 | Anderson | A61F 2/167 606/107 |
| 2014/0257315 A1* | 9/2014 | Wu | A61F 2/167 606/107 |
| 2014/0257317 A1* | 9/2014 | Safabash | A61F 2/1678 606/107 |
| 2014/0276901 A1* | 9/2014 | Auld | A61F 2/1678 606/107 |
| 2016/0074156 A1 | 3/2016 | Raquin et al. | |
| 2017/0172727 A1* | 6/2017 | Kanner | A61F 2/167 |
| 2018/0049866 A1* | 2/2018 | Fayyaz | A61F 2/167 |

* cited by examiner

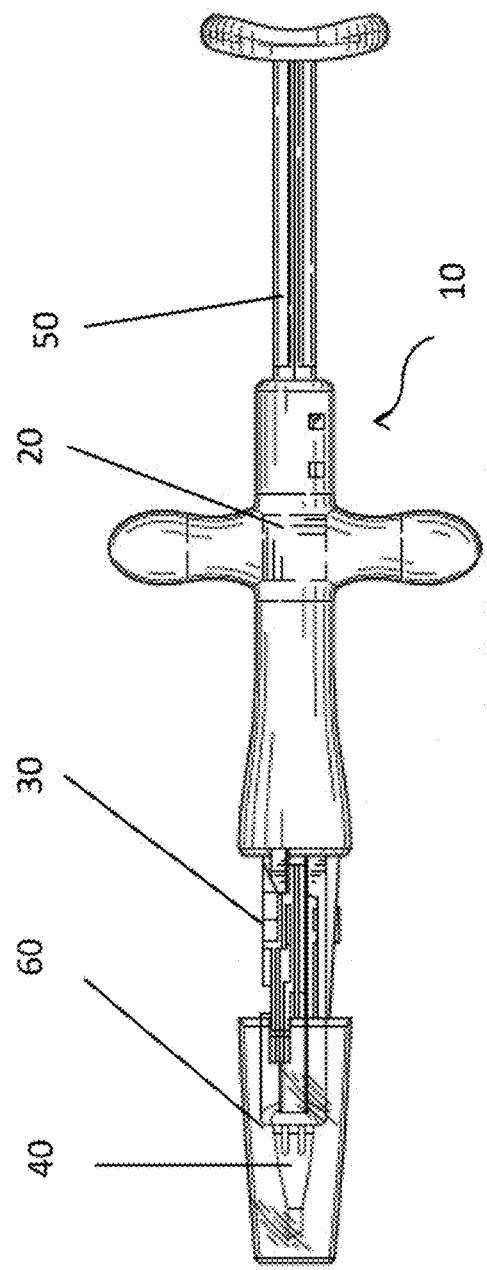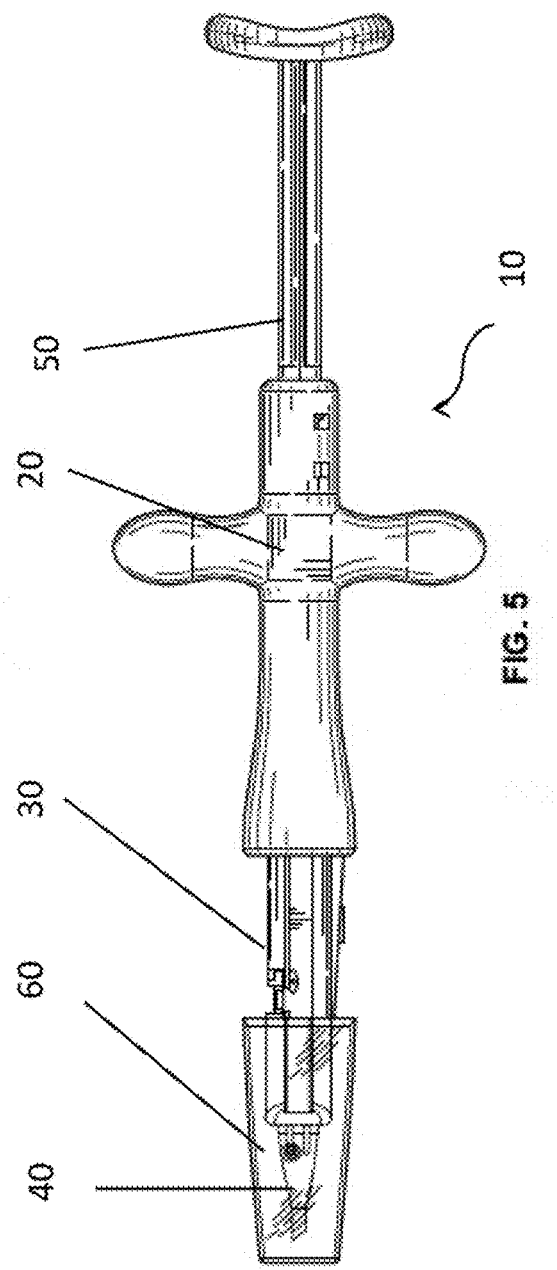

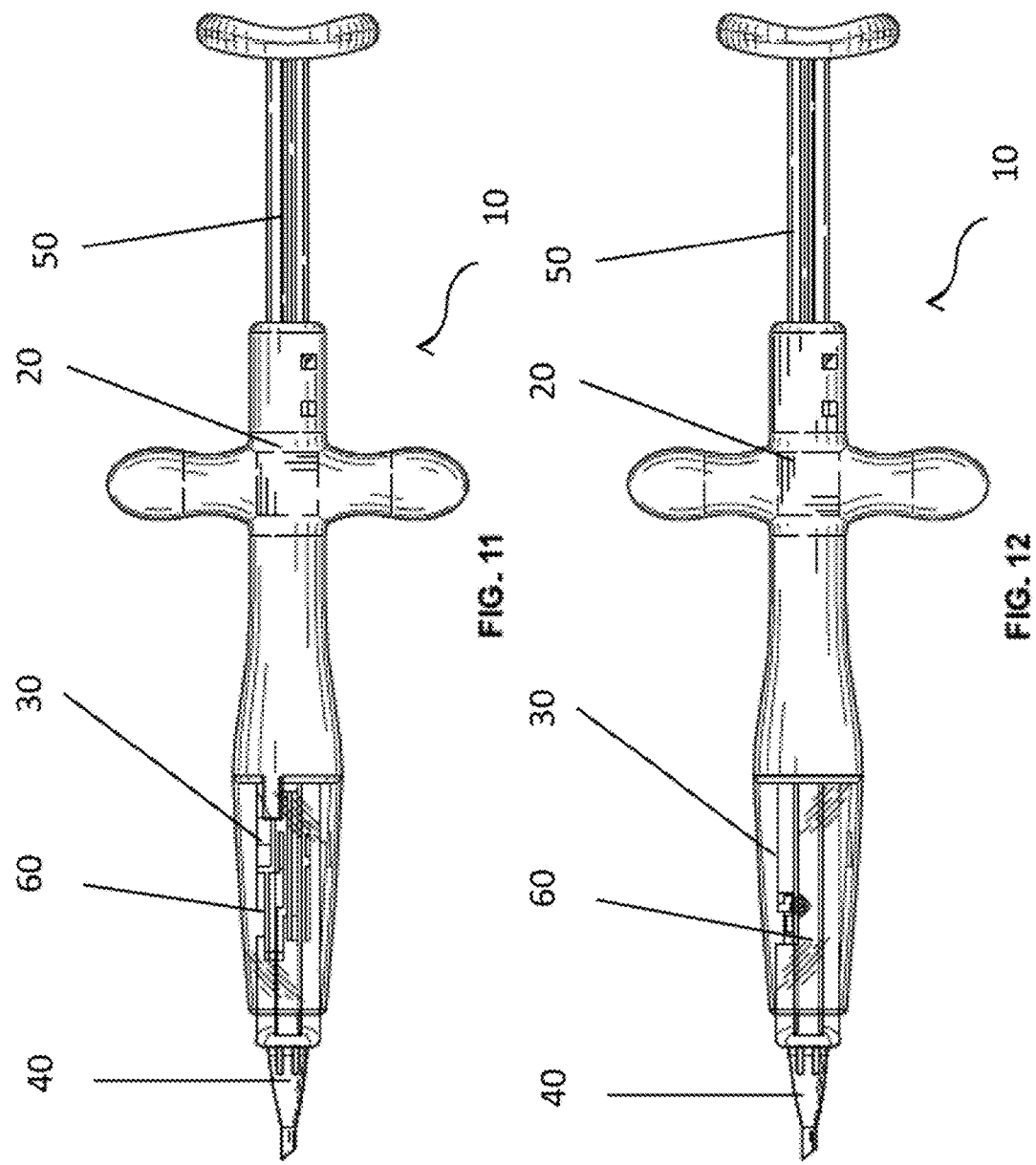

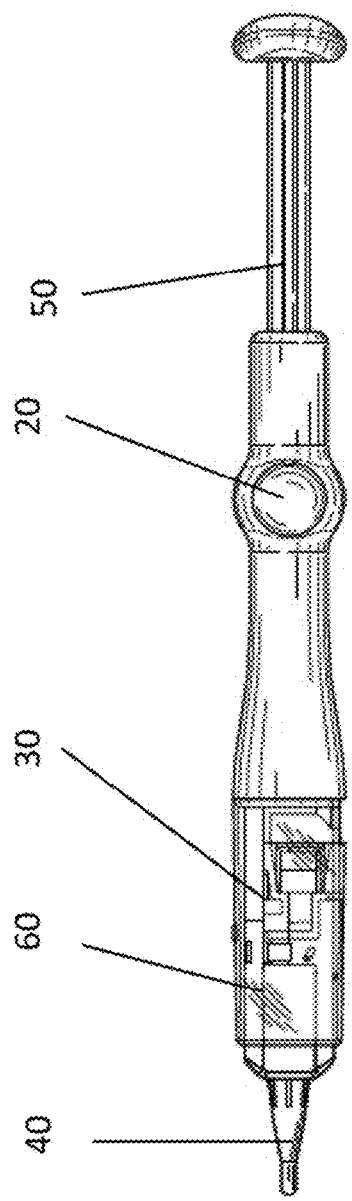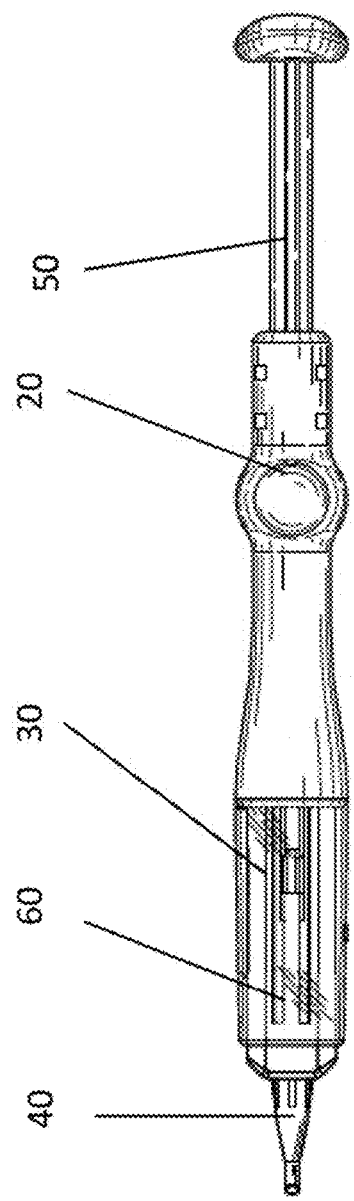

INTRAOCULAR LENS (IOL) INJECTOR AND METHOD OF USE THEREOF

BACKGROUND OF THE INVENTION

Field of the Invention

The invention relates generally to ophthalmic surgical devices and methods, and more particularly to a device and method for inserting an intraocular lens (IOL) into an eye of a patient.

Background Information

Intraocular lens (IOL) injectors are devices designed to insert an IOL into the eye of a patient. Such lenses are surgical implants designed to augment or replace the natural lens of the eye, and are used to treat certain diseases of the eye. For example, the impairment of vision caused by cataracts is often treated by the surgical removal and replacement of the eye's lens. During such a surgery a small 1-4 mm incision is formed in the patient's eye. The surgeon then uses a tool, inserted into the eye through the incision, to emulsify (break up) and remove the eye's natural lens. Once removed an artificial intraocular lens is inserted in the eye.

In order to insert the lens without enlarging the incision, lenses are employed which may be compressed or folded, and inserted through an incision, often using an injector device. Once the IOL is in the eye, it is designed to recover to its unfolded shape with a predetermined orientation within the eye. In this process, placement of the IOL is critical, especially for toric lenses used for treatment of astigmatism which require precise positioning and orientation at a predetermined location in the eye. Improper placement requires the surgeon to manually manipulate the IOL positioning which can cause damage to the eye, as well as damage to the IOL.

IOLs are typically transported and stored in a relaxed state to avoid damage to the lenses. As such, conventional injector devices require the physician to load the IOL into the injector thereby requiring the physician to exercise a great deal of skill in loading the IOL in the proper orientation while avoiding damage to the IOL. Conventional injector devices provide the physician with no ability to control orientation of a lens during loading and/or during delivery of a lens to the eye. As such, there exists a need for an improved IOL injector which is easier to use while ensuring proper deliver of an IOL to the eye.

SUMMARY OF THE INVENTION

The present invention addresses the deficiencies of conventional injectors by providing an IOL injector which is optionally preloaded with an IOL in the unfolded state, wherein the injector is configured to automatically fold and properly aligns the IOL during delivery of the IOL without relying on the skill of the physician.

Accordingly, in one aspect, the invention provides an IOL injector. The injector includes an injector body elongated along a longitudinal axis having a lumen disposed therein. A lens cartridge is in operable connection with the injector body and includes a lumen configured to receive an IOL and a positioning mechanism for folding and aligning the IOL in the lens cartridge lumen. An injector tip is in operable connection with the lens cartridge, the injector tip having a lumen which terminates in a distal opening. A plunger having an elongated shaft is slidably disposed in the lumen of the injector body. The plunger is configured to contact the folded IOL which is loaded in the lens cartridge lumen and push the IOL along the longitudinal axis through the injector tip lumen and out of the distal opening when the plunger is depressed into a deployed position. The injector further includes a sleeve in operable connection with the lens cartridge. The lens cartridge is configured to mechanically fold the IOL which is preloaded in the lens cartridge and align the IOL within the lens cartridge lumen via the positioning mechanism upon moving the sleeve over the lens cartridge from a distal first position where the sleeve is over the injector tip, to a proximal second position where the sleeve is over the lens cartridge.

In embodiments, the positioning mechanism includes a first and second cartridge portion which are mechanically moved toward one another perpendicular to the longitudinal axis of the device thereby folding the IOL when the sleeve is moved over the lens cartridge from the distal first position over the injector tip.

In another aspect, the invention provides a method of implanting an IOL using the injector device of the present invention. The method includes providing an IOL injector having an IOL preloaded in the lens cartridge, transitioning the sleeve from the distal first position over the injector tip, to the proximal second position over the lens cartridge thereby folding and aligning the IOL in the lens cartridge lumen, and depressing the plunger to transition it from the undeployed position to the deployed position to push the folded IOL along the longitudinal axis of the device and eject the IOL from the distal opening of the injector tip lumen into the eye of a patient.

In yet another aspect to the invention, the invention provides a kit for practicing the method of the invention. The kit includes an IOL injector of the invention and an IOL optionally preloaded in the injector. In embodiments, the injector is preloaded with the IOL such that the sleeve is in the distal first position and the IOL is in an unfolded state in the lens cartridge lumen.

BRIEF DESCRIPTION OF THE DRAWINGS

The present invention will be more readily understood from a detailed description of example embodiments taken in conjunction with the following figures:

FIG. 4 is a left side view of the IOL injector depicted in FIG. 1 in one embodiment of the invention;

FIG. 5 is a right side view of the IOL injector depicted in FIG. 1 in one embodiment of the invention;

FIG. 11 is a left side view of the IOL injector depicted in FIG. 8 in one embodiment of the invention;

FIG. 12 is a right side view of the IOL injector depicted in FIG. 8 in one embodiment of the invention;

FIG. 13 is a top view of the IOL injector depicted in FIG. 8 in one embodiment of the invention;

FIG. 14 is a bottom view of the IOL injector depicted in FIG. 8 in one embodiment of the invention;

DETAILED DESCRIPTION OF THE INVENTION

Figure 1:
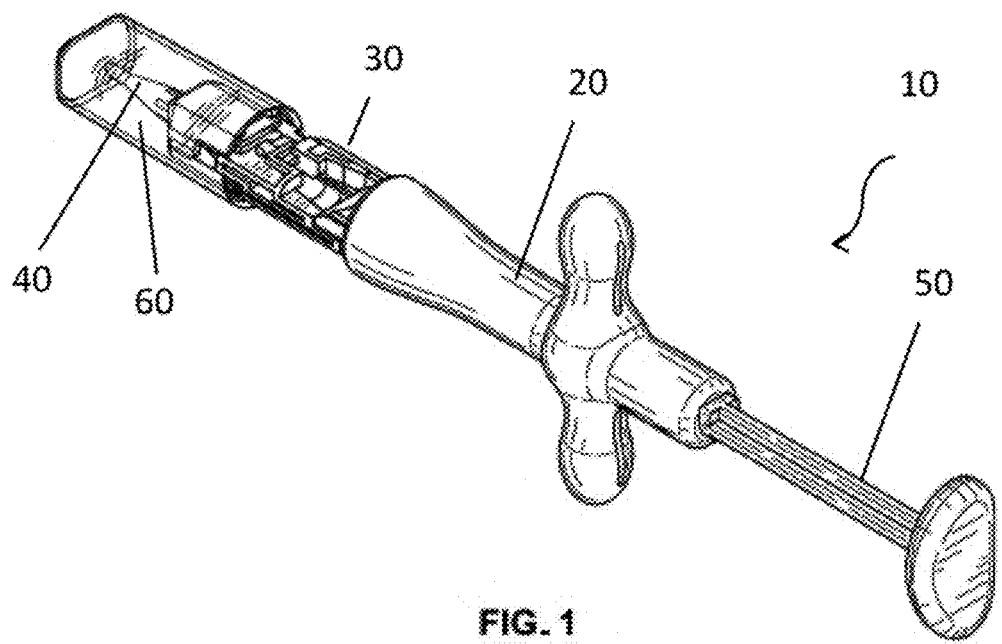
FIG. 1 is a perspective view of an IOL injector in one embodiment of the invention, wherein the sleeve 60 is in a first position covering the injector tip 40.
Figure 2:
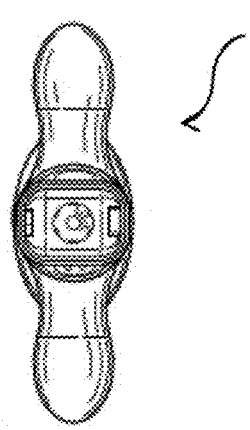
FIG. 2 is a front view of the IOL injector depicted in FIG. 1 in one embodiment of the invention.
Figure 3:
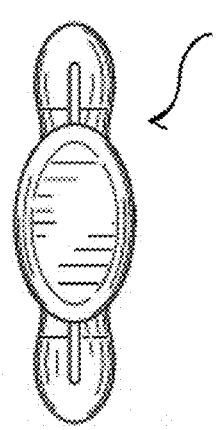
FIG. 3 is a back view of the IOL injector depicted in FIG. 1 in one embodiment of the invention.
Figure 6:
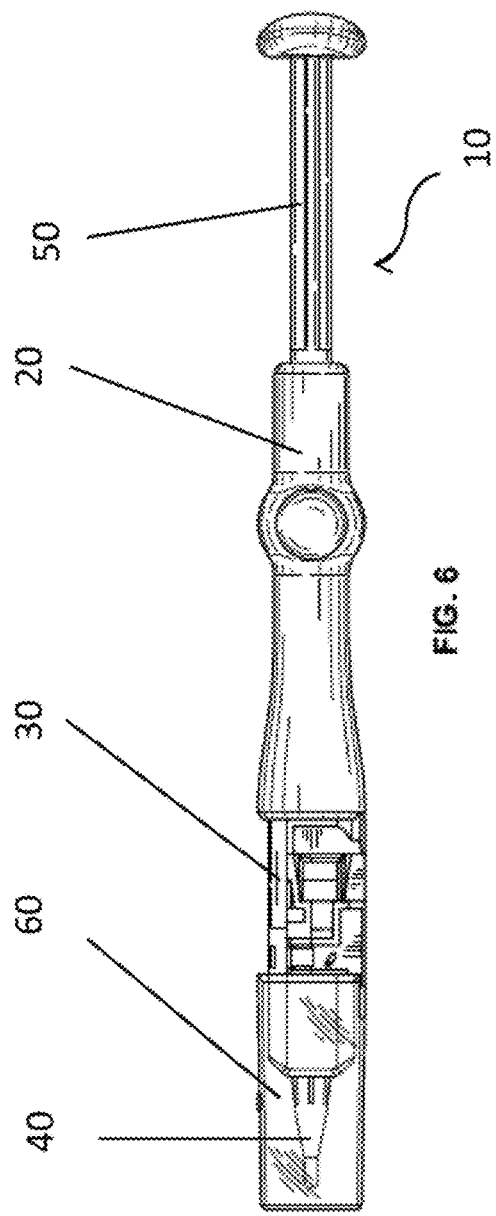
FIG. 6 is a top view of the IOL injector depicted in FIG. 1 in one embodiment of the invention.
Figure 7:
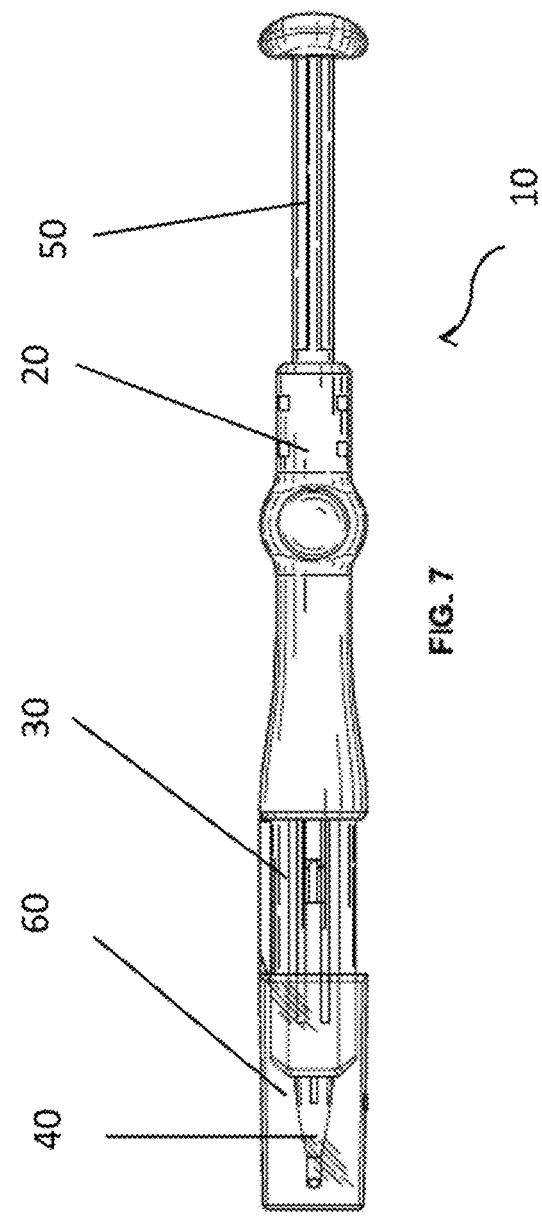
FIG. 7 is a bottom view of the IOL injector depicted in FIG. 1 in one embodiment of the invention.
Figure 8:
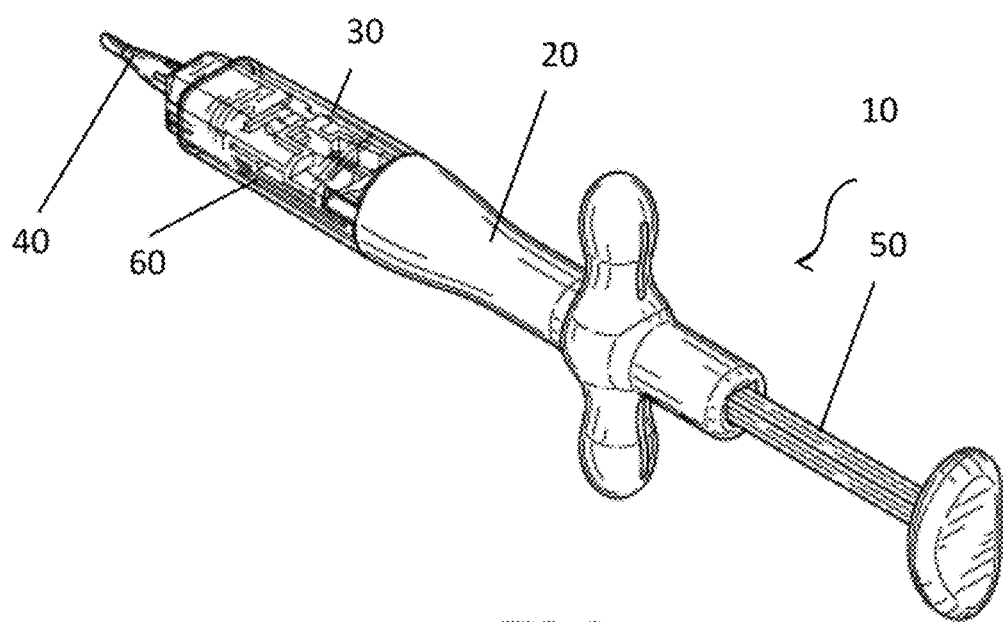
FIG. 8 is a perspective view of an IOL injector in one embodiment of the invention, wherein the sleeve 60 is in a second position covering the lens cartridge 30.
Figure 9:
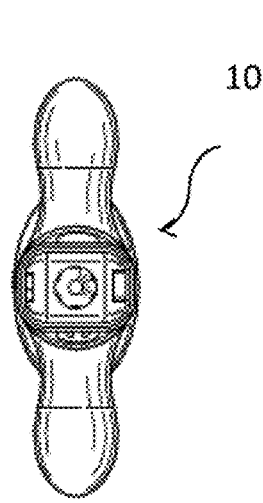
FIG. 9 is a front view of the IOL injector depicted in FIG. 8 in one embodiment of the invention.
Figure 10:
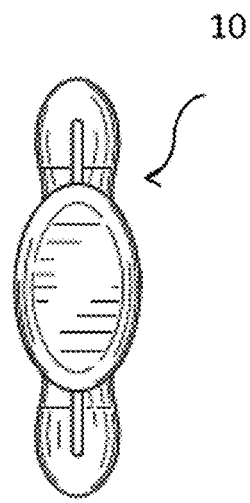
FIG. 10 is a back view of the IOL injector depicted in FIG. 8 in one embodiment of the invention.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In various aspects, the present invention provides a device and method for inserting an IOL into an eye of a patient. The IOL injector is configured to automatically load an IOL into the injector by folding and aligning the IOL into a lens cartridge of the injector without manual manipulation of the IOL by the physician during the procedure. The injector is configured to properly orient and align the IOL within the injector and maintain proper alignment throughout delivery of the IOL to the eye of a patient and thereby ensuring that the IOL is properly positioned and oriented at a predetermined location in the eye.

Referring to FIGS. 1 to 14, one such IOL injector 10 includes an injector body 20, a lens cartridge 30 in operable connection with the injector body, an injector tip 40 in operable connection with the lens cartridge, a plunger 50, and sleeve 60 in operable connection with the lens cartridge.

Figure 15:
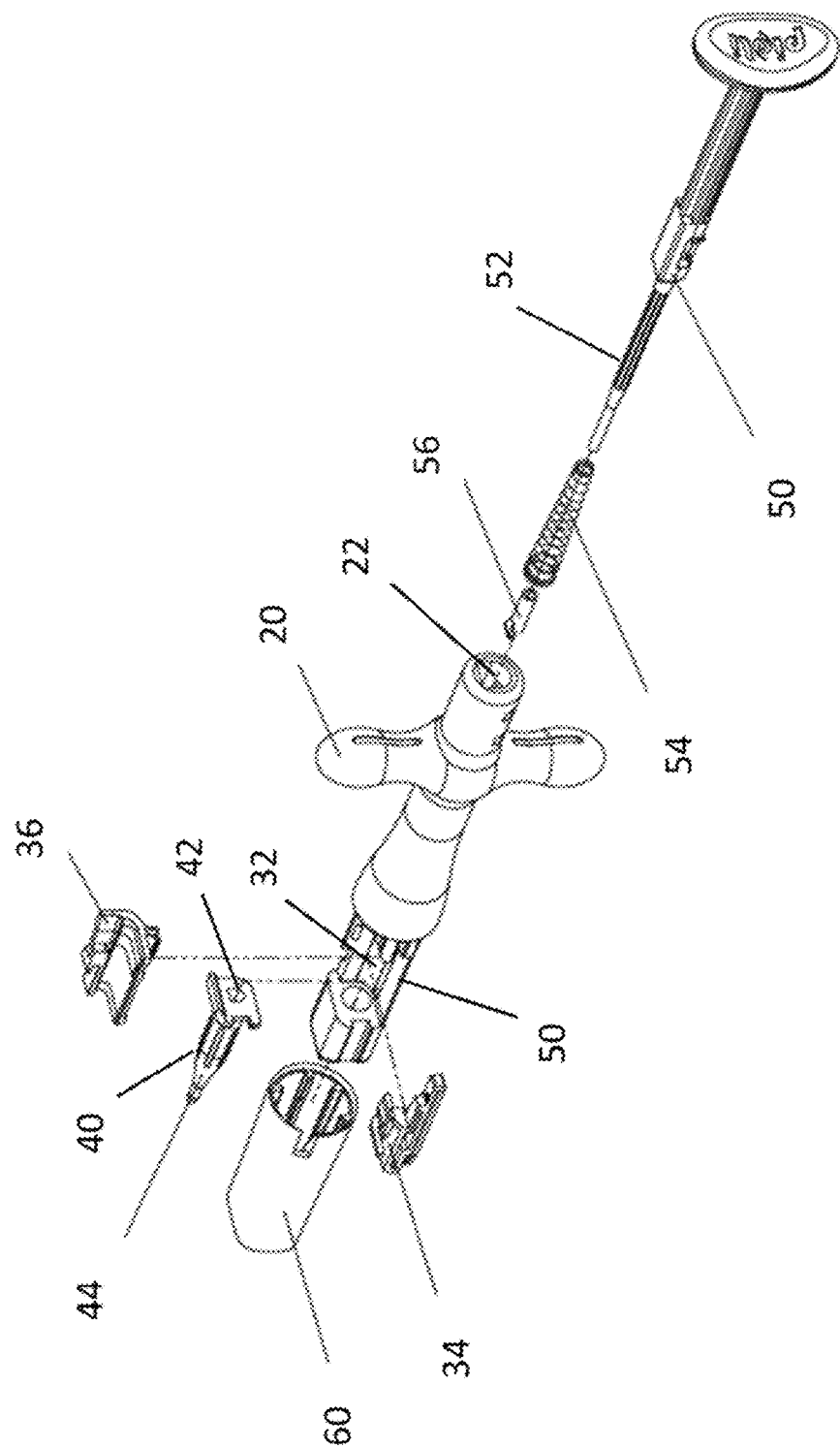
FIG. 15 is an exploded view of an IOL injector in one embodiment of the invention.

FIG. 15 is an exploded view showing the operable association of the components of the IOL injector. As illustrated, the plunger 50, the injector body 20, the lens cartridge 30, the injector tip 40 and sleeve 60 are arranged along a longitudinal axis of the IOL injector with the plunger being disposed on the proximal end of the injector and the injector tip 40 being disposed on the distal end of the injector. In embodiments, a lumen traverses the entire length of the device such that an IOL loaded into the lens cartridge lumen 32 can be pushed by the distal tip 56 of the elongated shaft 52 of the plunger 50 along the longitudinal axis through the injector tip lumen 42, and out of the distal opening 44 into a patient's eye, when the plunger 50 is advanced distally from an undeployed position to a deployed position.

As discussed herein, the injector is configured to mechanically fold and align the IOL within the lens cartridge such that the proper orientation is achieved upon loading of the IOL into the lens cartridge lumen as well as delivery to the eye. Folding and aligning of the IOL in the lens cartridge lumen is achieved via a positioning mechanism disposed in the lens cartridge 30 which is in operable connection to the sleeve 60. Transitioning the sleeve 60 from a first position in which the sleeve 60 covers the injector tip 40 as shown in FIGS. 1 to 7, to a second position in which the sleeve 60 covers the lens cartridge 30 as shown in FIGS. 8 to 14, causes the positioning mechanism to fold the IOL from a first unfolded state to a second folded state and align the IOL within the lens cartridge lumen 32. Once the IOL is folded and properly aligned within the lens cartridge lumen 32, the IOL may be delivered to a patient's eye by advancing the plunger 50 distally from an undeployed position to a deployed position.

Figure 16:
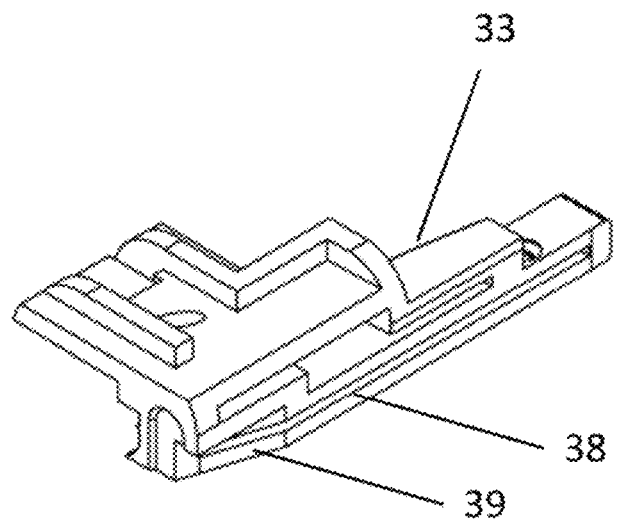
FIG. 16 is an expanded perspective view of the first cartridge portion 34 depicted in FIG. 15 in one embodiment of the invention.
Figure 17:
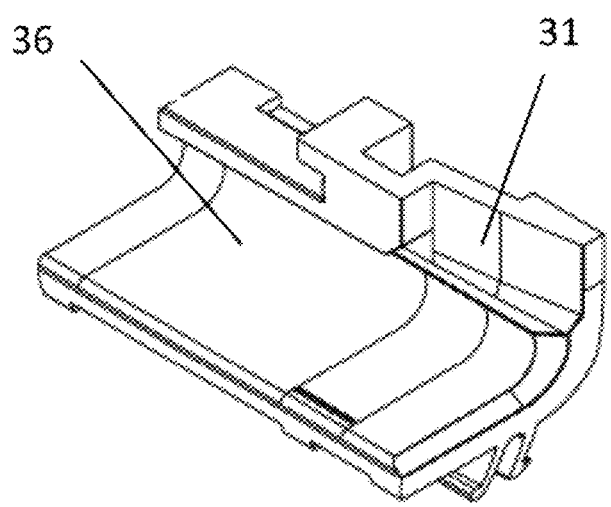
FIG. 17 is an expanded perspective view of the second cartridge portion 36 depicted in FIG. 15 in one embodiment of the invention.
Figure 18:
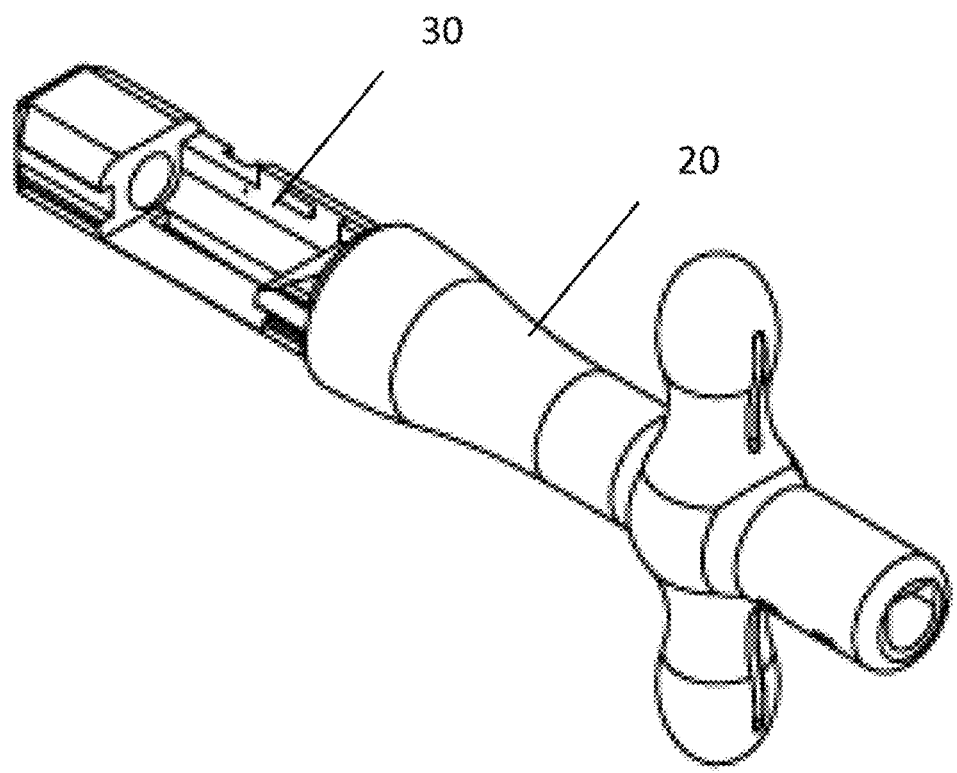
FIG. 18 is an expanded top perspective view of the injector body 20 and lens cartridge 30 depicted in FIG. 15 in one embodiment of the invention.

In embodiments, the positioning mechanism may include one or more components that operably associate to fold the IOL and interact with the sleeve 60. FIG. 15 illustrates an embodiment of the injector which includes a positioning mechanism having a first cartridge portion 34 and a second cartridge portion 36. The first cartridge portion 34 and the second cartridge portion 36 are illustrated in FIGS. 16 and 17, respectively. In this embodiment, the first cartridge portion 34 has a surface adapted to contact an internal surface of the sleeve and urge the first cartridge portion toward the second cartridge portion 36 when the sleeve 60 is moved from the first position to the second position. As illustrated in FIG. 16, surface 38 is configured to contact the internal surface of sleeve 60 as it moves from the first position to the second position. In the embodiment shown in FIG. 16, the surface 38 has a distal tapered region 39 which facilitates contact with the internal surface of the sleeve 60 as it is moved over the lens cartridge 30.

Figure 22:
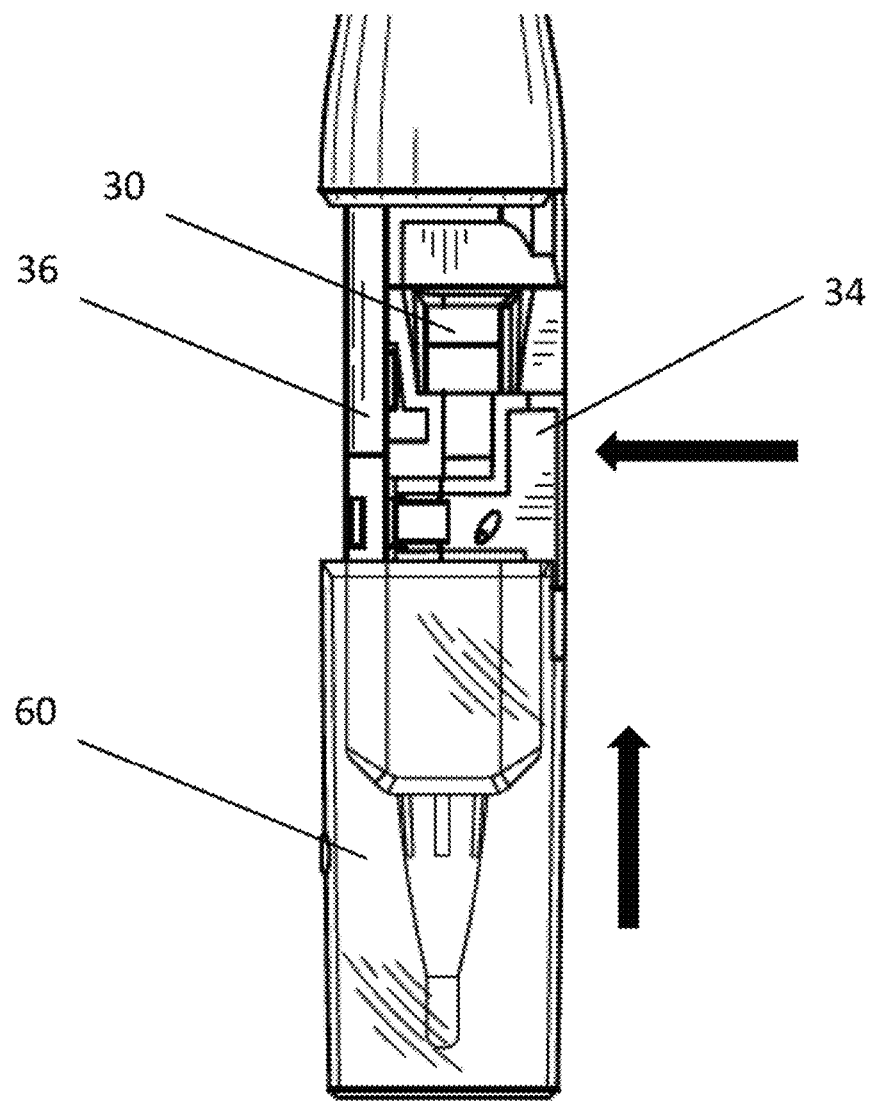
FIG. 22 is an expanded top view of the IOL injector depicted in FIG. 1 in one embodiment of the invention illustrating the distal region of the IOL injector.

As shown via arrows in FIG. 22, movement of the sleeve 60 from a first position (as depicted in FIG. 22) toward the lens cartridge 30 to a second position, in which the sleeve 60 covers the first and second cartridge portions (34 and 36), moves the first cartridge portion 34 inward perpendicular to the longitudinal axis of the device toward the second cartridge portion 36. Movement of the first cartridge portion 34 causes opposing surfaces disposed on the first and second cartridge portions (surfaces 31 and 33 as shown in FIGS. 16 and 17, respectively) to fold the IOL such the IOL is folded in half along the longitudinal axis of the injector. As such, in a folded state an IOL is essentially folded in half along its major dimension (i.e., length). In embodiments, where an IOL includes haptics, the injector is configured to position one or more of the haptics on the optic region of the IOL in the correct orientation for delivery. In one embodiment, a properly aligned IOL has a leading haptic pushed toward the optic and a trailing haptic contacting the distal tip 56 of the plunger 50. As such, a properly oriented IOL has the haptics "tagged" to the optical area. As will be recognized by one in the art, it is advantageous to construct the distal tip 56 using a material which will not damage the IOL upon contact. In embodiments, the distal tip 56 includes a polymeric material such as silicone, or other resiliently deformable polymer.

Figure 19:
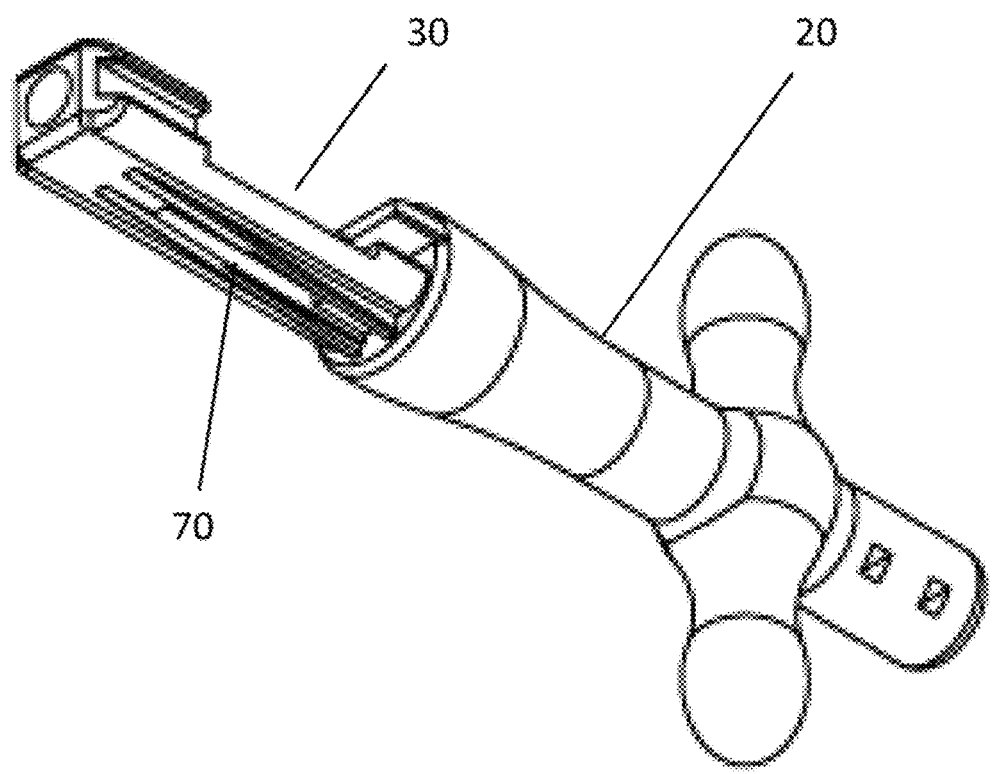
FIG. 19 is an expanded bottom perspective view of the injector body 20 and lens cartridge 30 depicted in FIG. 15 in one embodiment of the invention.
Figure 20:
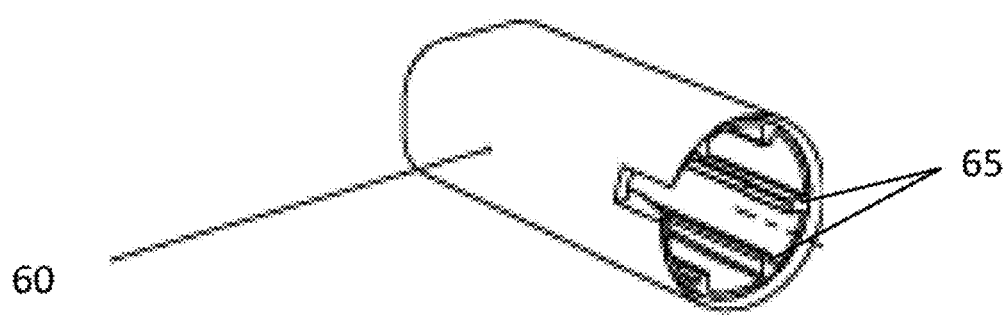
FIG. 20 is an expanded perspective view of the sleeve 60 depicted in FIG. 15 in one embodiment of the invention.

In embodiments, to facilitate alignment of the sleeve 60 with the lens cartridge 30, one or more raised ridge surfaces may be disposed on the internal surface of the sleeve. For example, FIG. 20 depicts an embodiment in which the internal surface of the sleeve includes multiple ridges 65 for interacting with corresponding grooves disposed on the lens cartridge 30. FIG. 19 illustrates an embodiment of a lens cartridge 30 having grooves 70 for receiving ridges disposed on the internal surface of the sleeve.

In certain aspects, the IOL injector is provided in a kit along with an IOL which is optionally preloaded in the lens cartridge of the injector. This reduces manual manipulation that is required by the physician in performing a surgical procedure thereby reducing the risk of contamination and damage to the IOL which can occur during handling of the IOL. Advantageously, providing the injector in a preloaded state, allows that injector to be sterilized with the IOL simultaneously at the factory during packaging. In embodiments where the injector is preloaded, the lens injector is provided with the IOL preloaded in the lens cartridge whereby the lens is in an unfolded state, the sleeve is in the first position covering the injector tip, and the plunger is in the undeployed state. Upon use, the physician simply needs to unpack the injector, transition the sleeve from the first position to the second position to fold and align the IOL in the lens cartridge, and deliver the IOL to the patient's eye by transitioning the plunger from the undeployed position to the deployed position. Further, the IOL injector may be configured for, single use such that the injector is discarded after delivery of the IOL to the eye.

Accordingly, in an aspect, the invention provides a method of implanting an IOL into the eye of a patient. The method includes providing an IOL injector of the invention having an IOL preloaded in the lens cartridge, transitioning the sleeve from the distal first position over the injector tip to the proximal second position over the lens cartridge thereby folding and aligning the IOL in the lens cartridge lumen, and depressing the plunger to transition it from the undeployed position to the deployed position to push the folded IOL along the longitudinal axis of the device and eject the IOL from the distal opening of the injector tip lumen into the eye of a patient.

In embodiments, the injector can be configured such that the sleeve can be locked in the second position. For example, the injector may include a locking mechanism which prevents movement of the sleeve from transitioning from the second position to the first position. This can be accomplished in a number of ways as will be appreciated by one in the art. For example, the locking mechanism may include a snap lock wherein the sleeve includes one or more locking structures which snap into corresponding recesses disposed on the lens cartridge.

As will be appreciated, the lumen extending along the longitudinal axis of the injector need not have a constant diameter. In embodiments, the lumen has a different diameter in different regions of the injector. For example, the lens cartridge lumen may have a different diameter than the injector tip lumen. In one embodiment, the diameter of the lens cartridge lumen is greater than the diameter of the injector tip lumen. Further, in embodiments, the injector tip lumen tapers from a larger diameter at the proximal end of the injector tip to a smaller diameter at the distal end of the injector tip where the distal opening is located.

In embodiments, the cross-sectional area of the injector tip lumen decreases from a larger diameter at the proximal end of the injector tip to a smaller diameter at the distal end of the injector tip where the distal opening is located. Additionally, the cross-sectional shape of the injector tip lumen may be different at the distal end of the injector tip lumen as compared to the proximal end of the injector tip lumen.

Figure 21:
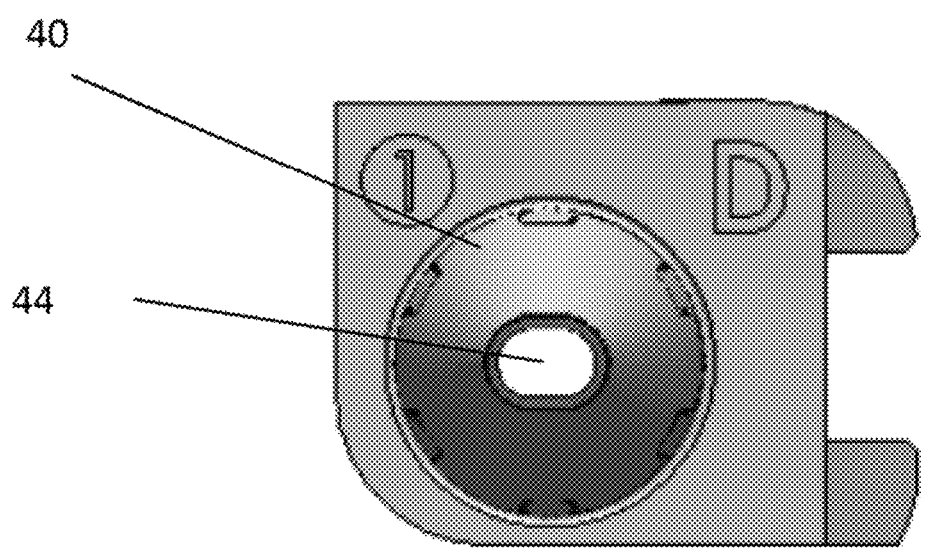
FIG. 21 is a front view of the injector tip 40 depicted in FIG. 15 in one embodiment of the invention.

FIG. 21 is a front view of an injector tip 40 showing an embodiment in which the distal opening 44 has an elongated circular cross-sectional shape. It will be appreciated that the cross-sectional shape of the distal opening can be any shape necessary to maintain proper folding and orientation of the IOL for delivery to the eye. This may depend in part on the type and shape of the IOL being delivered. For example, the cross-sectional shape of the distal opening can be square, round, ellipse, rectangle, triangle or curvilinear triangle.

The IOL injector may be constructed using a variety of different materials. One in the art will appreciate that different components of the injector may be constructed from different materials to impart different structural characteristics in different regions of the device. Further, various regions of the delivery lumen may include a polymer or lubricious coating.

Some embodiments of the present invention may provide IOL injectors with components constructed partially or entirely of polyurethane polymers; styrene related copolymers, such as but not limited to, polyolefin, polyamide, PEBAX, acrylic butyldiene styrene (ABS), styrene butyldiene styrene (SBS), and/or high impact polystyrene (HIPS); polyester polymers; and polymeric blends or copolymers thereof. Such materials may have sufficient toughness to enable the creation of small diameter insertion devices, and may also maintain or introduce other beneficial properties.

In order to ensure that the IOL is able to traverse the delivery lumen without causing damage to the lumen and/or the IOL, the delivery lumen should be able to withstand the application of the forces it will encounter during insertion. Accordingly, the delivery lumen may be formed from materials of sufficient toughness to withstand those forces without cracking or rupturing. In addition, in order to reduce the risk of damage to the IOL, and also reduce the insertion forces needed to perform the insertion, the delivery lumen may be formed of sufficiently lubricious material, be compounded with lubricating additives, be coated with a lubricating material, or otherwise minimize the forces tending to bind the IOL to the interior wall of the lumen. These considerations are especially true for the distal end of the injector tip since the tapering of the delivery lumen increases normal forces experienced by the delivery lumen as the IOL is moved distally.

In addition, in order to counter the frictional forces which may be experienced during the insertion process, in some embodiments a coating made of a hydrophilic polymeric material may be applied to the delivery lumen or lens cartridge to provide additional lubricity. For example, in some embodiments a coating may include one or more hydrophilic polymeric materials, such as but not limited to, hydrophilic polyurethane, polyvinylpyrrolidone, polyacrylic acid, polyacrylamides, polyhydroxyethyl methacrylate, and/or hyaluronan, or the like. It is noted, however, that the lubricants used in the delivery lumen need not be applied unifoimly along the lumen.

Additionally, some embodiments may utilize material formed using a co-molding process. Using such a process, two or more materials (e.g. polymers) may be extruded and/or injected to form a single piece, and may allow for the use of materials having different physical properties. For instance, materials may be used having both sufficient toughness and other desirable properties. For instance, a polyurethane may be used having sufficient toughness, while another polyurethane may be used having desirable lubrication properties.

In some embodiments, the injector is constructed using polymer compositions having engrafted hydrophilic and lubricious groups as described in U.S. Patent Application No. 2013/0129953 to Lee which is incorporated herein by reference. Such compositions utilize polypropylene, polycarbonate, polyimide, cellulose acetate, and acrylic polymer or copolymer which are suitable base polymers for engrafting.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Refractive Cataract Surgery Using IOL Injectors with Hydrophobic IOLs

Thirty (30) sets of the IOL injector of the present invention were used to deliver thirty (30) hydrophobic foldable single-piece intraocular lenses (IOLs) to simulate surgical manipulation during refractive cataract surgery. The 30 hydrophobic foldable single-piece intraocular lenses were consisted of IOLs of 10 low, 10 medium and 10 high diopters. All lenses were delivered through the injector of the present invention according to the loading and delivery procedure in the instructions for use.

The IOLs were evaluated for the optical properties, sagitta, and overall surface and bulk homogeneity before and after being surgically manipulated using the injector of the present invention, as well as lens opening time after folding. The injector of the present invention was also evaluated for its cartridge and tip performance, such as overall cartridge and tip surface and bulk homogeneity. IOL optical properties and overall surface and bulk homogeneity inspection were conducted in accordance with ISO 11979-2, Ophthalmic implants—Intraocular lenses—Part 2: Optical properties and test methods and ISO 11979-3, Ophthalmic implants—Intraocular lenses—Part 3: Mechanical properties and test methods.

After delivery, all lenses were observed for possible damages or scratches using a Nikon™ SMZ-1 Stereoscopic microscope. All delivered lenses showed no damages or scratches, and were within dimensional specifications. Also, all cartridges showed no damages after lens delivery. The resulting data from simulated surgical manipulation of the injector of the present invention to deliver hydrophobic intraocular lens showed that the injector of the present invention can successfully deliver hydrophobic IOLs of low, medium to high diopters without affecting the functionality of the lens.

Example 2

Refractive Cataract Surgery Using IOL Injectors with Hydrophilic IOLs

Thirty (30) sets of the injector of the present invention were used to deliver thirty (30) hydrophilic foldable single-piece intraocular lenses (IOLs) to simulate surgical manipulation during refractive cataract surgery. The 30 hydrophilic foldable single-piece intraocular lenses were consisted of IOLs of 10 low, 10 medium and 10 high diopters. All lenses were delivered through the injector of the present invention according to the loading and delivery procedure in the instructions for use.

The IOLs were evaluated for the optical properties, sagitta, and overall surface and bulk homogeneity before and after being surgically manipulated using the injector of the present invention, as well as lens opening time after folding. The injector of the present invention was also evaluated for its cartridge and tip performance, such as overall cartridge and tip surface and bulk homogeneity. IOL optical properties and overall surface and bulk homogeneity inspection were conducted in accordance with ISO 11979-2, Ophthalmic implants—Intraocular lenses—Part 2: Optical properties and test methods and ISO 11979-3, Ophthalmic implants—Intraocular lenses—Part 3: Mechanical properties and test methods.

After delivery, all lenses were observed for possible damages or scratches using a Nikon™ SMZ-1 Stereoscopic microscope. All delivered lenses showed no damages or scratches, and were within dimensional specifications. Also, all cartridges showed no damages after lens delivery. The resulting data from simulated surgical manipulation of the injector of the present invention to deliver hydrophilic intraocular lens showed that the injector of the present invention can successfully deliver hydrophilic IOLs of low, medium to high diopters without affecting the functionality of the lens.

Although the invention has been described with reference to the above examples, it will be understood that modifications and variations are encompassed within the spirit and scope of the invention. Accordingly, the invention is limited only by the following claims.

What is claimed is:

1. An intraocular lens (IOL) injector comprising:
   a) an injector body elongated along a longitudinal axis, the injector body having a lumen disposed along the longitudinal axis;
   b) a lens cartridge in operable connection with the injector body, the lens cartridge having a lumen configured to receive an IOL and a positioning mechanism for folding and aligning the IOL in the lens cartridge lumen, wherein the lens cartridge lumen is coextensive with the injector body lumen;
   c) an injector tip in operable connection with the lens cartridge, the injector tip having a lumen disposed along the longitudinal axis and terminating in a distal opening, wherein the injector tip lumen is coextensive with the injector body lumen;
   d) a plunger having an elongated shaft, the elongated shaft being slidably disposed within the injector body lumen from an undeployed position to a deployed position, wherein the plunger is configured to contact the IOL in the lens cartridge lumen and push the IOL along the longitudinal axis through the injector tip lumen and out of the distal opening when the plunger is transitioned to the deployed position; and e) a sleeve in operable connection with the lens cartridge, wherein the lens cartridge is configured to fold the IOL and align the IOL within the lens cartridge lumen via the positioning mechanism upon moving the sleeve over the lens cartridge from a first position to a second position, the sleeve covering at least a portion of the lens cartridge in the second position, wherein the positioning mechanism comprises a first cartridge portion having a surface adapted to contact an internal surface of the sleeve and urge the first cartridge portion toward a second cartridge portion when the sleeve is moved from the first position to the second position.

2. The IOL injector of claim 1, wherein the sleeve covers the entire lens cartridge and contacts the injector body in the second position.

3. The IOL injector of claim 1, wherein a surface of the injector tip lumen or the lens cartridge lumen comprises a polymer or lubricious coating.

4. The IOL injector of claim 3, wherein the lubricious coating is a hydrophilic and lubricious polymer or copolymer matrix.

5. The IOL injector of claim 1, wherein the IOL is folded in half along the longitudinal axis when the sleeve is in the second position.

6. The IOL injector of claim 1, wherein the surface of the first cartridge portion has a tapered region.

7. The IOL injector of claim 6, wherein the surface of the tapered region is angled with respect to the longitudinal axis.

8. The IOL injector of claim 1, wherein the second cartridge portion has a recess adapted to receive a raised internal surface of the sleeve.

9. The IOL injector of claim 1, wherein the distal opening of the injector tip lumen is a geometric shape selected from the group consisting of square, round, ellipse, rectangle, triangle, curvilinear triangle.

10. The IOL injector of claim 1, wherein the injector tip lumen has a proximal region having an opening, wherein the cross sectional area of the opening is greater than the cross section area of the distal opening.

11. The IOL injector of claim 1, wherein the plunger further comprises a spring disposed over the elongated shaft.

12. The IOL injector of claim 1, wherein the first cartridge portion and the second cartridge portion form a slot for accessing the lens cartridge lumen in the first position.

13. The IOL injector of claim 12, wherein the slot is configured to receive the IOL when the thickness of the IOL is perpendicular to the longitudinal axis.

14. The IOL injector of claim 1, further comprising a locking mechanism configured to secure the sleeve in the second position.

15. The IOL injector of claim 14, wherein the locking mechanism comprises one or more slots disposed on the lens cartridge or the injector body configured to receive one or more locking structures disposed on the sleeve.

16. A method of implanting an intraocular lens (IOL), comprising:

a) providing an IOL injector, the injector comprising:
  i) an injector body elongated along a longitudinal axis, the injector body having a lumen disposed along the longitudinal axis;
  ii) a lens cartridge in operable connection with the injector body, the lens cartridge having a lumen configured to receive an IOL and a positioning mechanism for folding and aligning the IOL in the lens cartridge lumen, wherein the lens cartridge lumen is coextensive with the injector body lumen;
  iii) an injector tip in operable connection with the lens cartridge, the injector tip having a lumen disposed along the longitudinal axis and terminating in a distal opening, wherein the injector tip lumen is coextensive with the injector body lumen;
  iv) a plunger having an elongated shaft, the elongated shaft being slidably disposed within the injector body lumen from an undeployed position to a deployed position, wherein the plunger is configured to contact the IOL in the lens cartridge lumen and push the IOL along the longitudinal axis through the injector tip lumen and out of the distal opening when the plunger is transitioned to the deployed position; and
  v) a sleeve in operable connection with the lens cartridge, wherein the lens cartridge is configured to fold the IOL and align the IOL within the lens cartridge lumen via the positioning mechanism upon moving the sleeve over the lens cartridge from a first position to a second position, the sleeve covering at least a portion of the lens cartridge in the second position, wherein the positioning mechanism comprises a first cartridge portion having a surface adapted to contact an internal surface of the sleeve and urge the first cartridge portion toward a second cartridge portion when the sleeve is moved from the first position to the second position; and b) inserting an IOL into the lens cartridge lumen when the sleeve is in the first position and the plunger is in the undeployed position;

c) transitioning the sleeve from the first position to the second position thereby folding and aligning the IOL in the lens cartridge lumen; and d) transitioning the plunger from the undeployed position to the deployed position thereby ejecting the IOL from the distal opening of the injector tip lumen into the eye of a patient, the IOL being in a folded state while exiting the distal opening.

17. The method of claim 16, wherein the second cartridge portion has a recess adapted to receive a raised internal surface of the sleeve.

18. A kit comprising:
a) the IOL injector of claim 1; and
b) an IOL.

19. The kit of claim 18, wherein the IOL comprises an optic and at least one haptic extending in a curved shape from the optic.

20. The kit of claim 18, wherein the injector is preloaded with the IOL such that the sleeve is in the first position and the IOL is in an unfolded state in the lens cartridge lumen.

* * * * *